United States Patent
Basso et al.

(10) Patent No.: US 10,745,734 B2
(45) Date of Patent: Aug. 18, 2020

(54) **ENRICHMENT AND SELECTIVE CULTURE OF *SALMONELLA* AND *SHIGELLA***

(71) Applicant: BIOMERIEUX, Marcy L'etoile (FR)

(72) Inventors: Emanuelle Basso, Montrottier (FR); Jean-Marc Roche, Feissons sur Salins (FR)

(73) Assignee: BIOMERIEUX, Marcy l'Etoile (FR)

( * ) Notice: Subject to any disclaimer, the term of this patent is extended or adjusted under 35 U.S.C. 154(b) by 88 days.

(21) Appl. No.: 15/573,511

(22) PCT Filed: May 11, 2016

(86) PCT No.: PCT/FR2016/051102
§ 371 (c)(1),
(2) Date: Nov. 13, 2017

(87) PCT Pub. No.: WO2016/181070
PCT Pub. Date: Nov. 17, 2016

(65) Prior Publication Data
US 2018/0142278 A1  May 24, 2018

(30) Foreign Application Priority Data
May 12, 2015  (FR) ..................... 15 54223

(51) Int. Cl.
| | | |
|---|---|---|
| *C12Q 1/04* | (2006.01) | |
| *C12Q 1/10* | (2006.01) | |
| *C12N 1/20* | (2006.01) | |
| *C12P 13/10* | (2006.01) | |
| *C12R 1/42* | (2006.01) | |

(52) U.S. Cl.
CPC .............. *C12Q 1/045* (2013.01); *C12N 1/20* (2013.01); *C12P 13/10* (2013.01); *C12Q 1/10* (2013.01); *C12R 1/42* (2013.01); *C12Q 2334/00* (2013.01); *G01N 2333/255* (2013.01); *G01N 2333/918* (2013.01); *Y02A 50/451* (2018.01)

(58) Field of Classification Search
CPC ...... C12Q 1/045; C12Q 2334/00; C12R 1/42; C12P 13/10; G01N 2333/918; G01N 2333/255; Y02A 50/451
See application file for complete search history.

(56) References Cited

PUBLICATIONS

Viala et al., PloS ONE, 2011, vol. 6, Issue 7, e22397, p. 1-12.*
IFU catalog, XLD AGAR, Hardy retrieved from Diagnostics.com, 1996, 6 pages of PDF.*
IFU catalog, XLT-4 AGAR, Hardy retrieved from Diagnostics.com, 1996, 5 pages of PDF.*
"Ornithine Decarboxylase Broth." Himedia-Techinal Data, XP002752826, 2011.
"Decarboxylase Differential Media." Difco&BBL Manual, 2nd Edition, XP002752827, 2009.
MacWilliams, Maria. "Indole Test Protocol." pp. 1-11, XP002752828, 2013.
"Moeller Decarboxylase Broth with Omithine HCl (DM468)." Micromaster, Product Specification Sheet, pp. 1-4, XP002752829, 2008.
Arroyo et al. "Selective action of inhibitors used in different culture media on the competitive microflora of *Salmonella*." Journal of Applied Bacteriology, Blackwell Publishing Ltd., vol. 78, No. 3, pp. 281-289, XP002555076, 1995.
Sep. 21, 2016 Search Report issued in International Patent Application No. PCT/FR2016/051102.
Sep. 21, 2016 Written Opinion issued in International Patent Application No. PCT/FR2016/051102.

* cited by examiner

*Primary Examiner* — Kade Ariani
(74) *Attorney, Agent, or Firm* — Oliff PLC

(57) ABSTRACT

What is disclosed relates to the detection and identification of bacteria of the genera *Salmonella* and *Shigella*. It relates more precisely to the methods of microbiology and the culture media used for the detection, identification, isolation and/or analytical investigation of these bacteria. Relating to a method for enrichment and selective culture of bacteria of the genera *Salmonella* and/or *Shigella* contained in a biological sample. In the method, some or all of the sample is seeded in/on a culture medium including a nutrient component that favors the development and growth of the bacteria, and includes L-ornithine as a selective agent. It also covers a culture medium suitable for carrying out this method.

7 Claims, No Drawings

ENRICHMENT AND SELECTIVE CULTURE OF *SALMONELLA* AND *SHIGELLA*

The present invention relates to the detection and identification of bacteria of the genera *Salmonella* and *Shigella*. More precisely, it relates to the methods of microbiology and the culture media used for the detection, identification, isolation and/or analytical investigation of these bacteria.

Belonging to the Enterobacteriaceae family, salmonellae and shigellae are bacteria that are human pathogens. Transmissible to humans after ingestion of water and/or foodstuffs contaminated with feces of animal or human origin, they cause diseases and digestive disorders that may have sequelae that are irreversible, and sometimes lethal.

With regard to salmonellae, these bacteria are generally transmitted to humans through ingestion of water and/or foodstuffs contaminated with animal feces.

Apart from *Salmonella typhi* and *Salmonella paratyphi*, the salmonellae are responsible for salmonellosis, an inflammatory infection of the alimentary canal that causes abdominal cramps, diarrhea, fever and nausea. These symptoms appear very soon after contamination (generally, after 8 to 72 hours of incubation). Without particular treatment, remission generally occurs after four to seven days. For persons at risk (in particular, immunodepressed patients, infants, the elderly, pregnant women), antibiotic treatment is recommended to prevent any serious, or even lethal complication: severe diarrhea and dehydration requiring hospitalization, gastrointestinal hemorrhage, intestinal perforation, pneumonia, acute gallbladder infection, hepatitis, and septicemia that may lead to generalized infection (bones, heart, brain, kidneys, etc.).

The much more virulent species *Salmonella Typhi* and *Salmonella Paratyphi* are responsible for typhoid fever and paratyphoid fever. These bacteria develop firstly at the level of the subject's intestinal lymph nodes, then cross the intestinal wall before reaching the bloodstream, where they release their toxins. A continuous fever then ensues, generally one to three weeks after contamination. This fever is accompanied by headaches, anorexia, exhaustion, abdominal pains and diarrhea or constipation. In the benign forms, the subject's condition remains steady for about a fortnight, and is then followed by convalescence for several weeks. In the more serious forms, complications develop at the level of the small intestine (where perforations may occur) and may affect the bladder, heart, joints, nervous system, etc. infection may prove fatal if the subject does not quickly receive appropriate antibiotic treatment.

Regarding shigellae, these bacteria are generally transmitted to humans through ingestion of water and/or foodstuffs contaminated with human feces (from chronic carriers or patients with shigellosis). They are responsible for shigelloses, bacillary dysentery caused by an inflammatory infection of the large intestine.

In contrast to other less severe diarrheic diseases, cure of the subject is not spontaneous and requires more than rehydration. In a great many cases, therapeutic treatment with antibiotics gives rapid remission, without sequelae.

Among the shigellae, *Shigella dysenteriae* appears to the most virulent species. It is the only one that releases exotoxins. It causes destruction of the infected tissues and acute, glairy, bloody diarrhea.

Each year, shigelloses are said to kill between six hundred thousand and a million people worldwide, mainly children under 5 years.

From the clinical standpoint, early diagnosis of infections by salmonellae and shigellae is of great importance, and would allow formulation of a therapeutic solution suitable for the patients.

Unfortunately the first symptoms associated with infection by these bacteria can be mistaken for those of simple indigestion or a common gastrointestinal, diarrheic disorder (in this case abdominal cramps, nausea, vomiting, fever, diarrhea). Thus, bacteriological examination of stool samples (SES) is prescribed by the practitioner since the presence of a germ that is dangerous for the patient's health is suspected.

In this respect, several culture media are known that are favorable to the development and growth both of *Salmonella* and of *Shigella*. As examples, we may mention the media of the BO) ("BroinCresol Purple") agar type, deoxycholate agars, Hektoen agar, "GN Broth" (broth according to Hajna), *Salmonella-Shigella* Agar (or SS Agar), MacConkey agar No, 3, XII) ("Xylose Lysine Deoxycholate") agar, DCLS ("Deoxycholate Citrate lactose Sucrose") agar.

The composition and the formulation of these media are described notably in the HANDBOOK OF MICROBIOLOGICAL MEDIA (2010; 4th Edition).

These media make it possible to meet the nutritional needs of the microorganisms to be cultured. Broadly, their composition includes:
- water (generally distilled or deionized water);
- at least one carbohydrate, as a carbon-containing energy source; it is generally glucose (optionally in the form of sucrose or salicin) and/or lactose;
- as well as other nutrients (notably amino acids, growth factors, vitamins, minerals, trace elements, iron citrate, sodium citrate, sodium chloride, etc.) supplied in the form of chemically complex compositions such as mixtures of peptones (from milk, meat and/or potato starch and/or corn starch, etc.), yeast extracts, serum extracts, and/or extracts of tissues of animal and/or vegetable origin, etc.
- also various salts, for example sodium chloride, to give the medium suitable osmolarity.

Moreover, these media may display a certain selectivity with respect to salmonellae and shigellae, owing to the use of selective agents, at least partly inhibiting the accompanying flora (i.e. bacteria other than salmonellae and shigellae). For this reason, in order to inhibit the Gram-positive bacteria, the following are used conventionally:
- sodium deoxycholate,
- bile salts,
- crystal violet, and
- brilliant green.

Some of these media are also discriminating and contain, for this purpose, a chromogenic and/or fluorogenic component allowing visual detection, and optionally visual identification, of the microorganisms according to the particular metabolic activities that they express. They may be, for example:
- pH color indicators (for example neutral red, phenol red, bromocresol purple, the pair bromothymol blue and acid fuchsin), which make it possible to label, with a distinctive stain, the colonies of microorganisms that ferment at least one of the carbohydrates present in the medium (for example glucose, sucrose, lactose and/or salicin) from the other bacteria;
- a sodium thiosulfate/iron(III) citrate system, which allows detection of the $H_2S$-producing bacteria (in this case, the salmonellae), the latter then appearing in the form of colonies with a black center, chromogenic and/or fluorogenic substrates allowing the detection of particular enzyme activities.

Despite this great diversity, the culture media currently available all have the drawback of relatively low sensitivity and selectivity, when they are used in the context of bacteriological examination of stool samples, for purposes of enrichment and simultaneous detection of *Salmonella* and *Shigella*.

These drawbacks can be explained essentially by the presence of intestinal/enteric microbial flora that is extremely abundant and varied (millions of microorganisms per gram of stool, covering numerous bacterial and fungal species), which far outnumber the salmonellae and shigellae. Once seeded on/in the conventional culture media, any salmonellae and shigellae present in the test sample are not only physically obscured by this accompanying flora, but the latter also interfere with their growth and development, thus further delaying their detection.

The detection and identification of salmonellae and shigellae on these culture media is also made difficult by considerable metabolic and physiological similarity with other intestinal bacteria.

Thus, in spite of the great variety of culture media currently proposed for detecting *Salmonella* and *Shigella* in feces, there is still a need for further improvement of their sensitivity and selectivity, and for shortening the time taken for detection as much as possible. The present application aims to address these needs.

More generally, the present invention aims to improve the methods and techniques used for detecting, identifying and/or isolating the bacteria of the genera *Salmonella* and *Shigella*. Moreover, it aims to propose novel compositions of culture media and/or enrichment broths, suitable for culture and multiplication of the bacteria of the genera *Salmonella* and *Shigella*, and having improved performance with respect to selectivity.

Before describing the invention, the following definitions are given to allow better understanding of the invention.

"Culture medium" means a medium comprising all the elements necessary for expression of metabolism and/or for the growth of microorganisms. The culture medium may be liquid, solid, or semisolid. "Solid medium" or "semisolid medium" means for example a gelled medium. Agar is the traditional gelling agent in microbiology for culture of microorganisms, but it is possible to use gelatin, agarose or other natural or artificial gelling agents. The "solid" or "semisolid" character of the media depends essentially on the content of gelling agent. For simplicity, the expression "solid medium" will be used hereinafter to denote both a solid medium and a semisolid medium.

"Enrichment broth" denotes more specifically a liquid culture medium.

A culture medium is described as a minimum medium when its composition comprises only the chemical elements strictly necessary for growth and multiplication of the microorganisms to be cultured. Classically they include:
  water (generally distilled or deionized water);
  a nutrient component generally comprising:
    a carbon-containing energy source (generally glucose and/or lactose);
    a source of calcium (for example $CaCl_2$);
    a source of nitrogen (for example $(NH_4)_2SO_4$);
    a source of sulfur (for example $(NH_4)_2SO_4$);
    a source of magnesium (for example $MgCl_2$);
    a source of iron (for example iron citrate);
    a source of trace elements (for example salts of Cu, Zn, Co, Ni, B, Ti);
  optionally a pH buffer for keeping the medium at an appropriate pH;
  optionally various salts, at a suitable concentration level to endow the medium with a suitable osmolarity; and
  for solid media, optionally a gelling agent (for example agar, gelatin or agarose).

Addition of particular growth factors and/or various nutrients makes it possible to reinforce the attributes of the nutrient component and increase the fertility of the medium. It is then called an "enriched" medium. Addition of these growth factors and/or nutrients may be effected by means of chemically defined compounds or compositions, or else by means of complex compositions (for example, fresh blood, sera, yeast extract, peptones, etc.).

A culture medium is said to be "selective" when it comprises at least one selective agent allowing said medium to favor the growth of a target microorganism or of a target group of microorganisms, rather than of the accompanying flora. This essentially comprises compounds with antibiotic and/or antifungal effects, and displaying specificity of toxicity (toxicity that is lower for the target microorganisms than for the accompanying flora).

"Biological sample" means a clinical sample obtained from a sample of human or animal origin (in particular, a stool sample), or a food sample from any type of food (for example meat, egg, vegetables, mayonnaise, cheese, fish, drinks such as milk, fruit juice, water, etc.). This biological sample may be liquid or solid. To simplify the vocabulary, the expressions "sample" and "sample taken" will be used indifferently.

The present invention thus relates to a procedure (a method) for enrichment and selective culture of bacteria of the genera *Salmonella* and/or *Shigella* contained in a biological sample, wherein a part or the Whole of said sample is seeded in on a culture medium comprising a nutrient component that favors the development and growth of said bacteria, characterized in that said culture medium also comprises L-ornithine, as a selective agent.

The present invention is based on the general principle of incorporating L-ornithine in compositions of culture media intended for the culture of *Salmonella* and/or *Shigella*, to increase their selectivity with respect to these bacteria, at the expense of the accompanying flora, which is at least partly inhibited.

Advantageously, the L-ornithine concentration in the culture medium used for carrying out the method of enrichment and selective culture according to the invention is above 10 g/L, and is preferably less than or equal to 25 g/L. According to a particular embodiment, this concentration is advantageously between about 15 g/L and about 20 g/L.

According to a preferred embodiment of the invention, said cults e medium further comprises at least one additional selective agent selected from:
  sodium deoxycholate, notably at a concentration between 0.1 g/L and 20 g/L, and even more preferably between about 1 g/L and about 10 g/L,
  Tergitol 4, notably at a concentration between 0.5 mL/L, and 10 mL/L, and even more preferably between about 1 mL/L and about 5 mL/L,
  bile salts, notably at a concentration between 0.1 g/L and 10 g/L, and even more preferably between about 0.5 g/L, and 5 g/L,
  crystal violet, notably at a concentration between 0.05 mg/L and 50 mg/L, and even more preferably between about 0.1 mg/L and about 10 mg/L, brilliant green, notably at a concentration between 1 mg/L and 200 ing/L, and even more preferably between 10 mg/L and 50 mg/L.

Advantageously, according to the invention, said culture medium further comprises, as selective agents:
- L-ornithine, at a concentration between about 15 g/L and about 20 g/L,
- sodium deoxycholate, at a concentration between about 1 g/L. and about 10 g/L, and
- optionally, Tergitol 4, at a concentration between about 0.5 mL/L, and about 5 mL/L.

According to an advantageous embodiment of the invention, said culture medium is a discriminating medium. In particular, the latter comprises at least one chromogenic component selected from:
- a pH color indicator (for example neutral red, phenol red, bromocresol purple, the pair bromothymol blue and acid fuchsia) capable of labeling the colonies of microorganisms fermenting at least one of the carbohydrates present in the medium;
- a sodium thiosulfate/iron(III) citrate system, allowing detection of the $H_2S$ producing bacteria;
- chromogenic and/or fluorogenic substrates allowing the detection of particular enzyme activities.

According to a particular aspect, the present invention aims to improve the methods for culturing and/or isolating bacteria of the genera *Salmonella* and/or *Shigella* that are commonly used at present, by adapting the composition of the usual culture media to increase their selectivity by inhibiting the accompanying flora. For this purpose, the present invention proposes to perfect the composition of these culture media, by supplying L-ornithine and, optionally, by supplying other selective agents as stated above.

In this context, the method of enrichment and selective culture according to the invention is advantageously carried out with a culture medium whose nutrient component repeats that of a culture medium selected from:
- XLD Agar (bioMérieux, France),
- chromID® *Salmonella* Elite Agar (bioMérieux, France),
- *Salmonella-Shigella* Agar (bioMérieux, France).

According to an even more preferred embodiment, the method of enrichment and selective culture according to the invention is carried out with a culture medium comprising a nutrient component and a selective component repeating those of XLD Agar, and supplemented with:
- L-ornithine, at a concentration between about 15 g/L, and about 20 g/L,
- optionally, X-beta-ribofuranoside, at a concentration between about 10 mg/L and about 200 mg/L,
- optionally, an opacifier such as titanium dioxide ($TiO_2$), notably at a concentration between about 0.1 g/L and about 5 g/L,
- optionally, Tergitol 4, at a concentration between about 0.5 mL/L and about 5 mL/L.

The present invention also covers a culture medium suitable for carrying out a method for enrichment and selective culture of bacteria of the genera *Salmonella* and *Shigella*. In the present case, a culture medium according to the invention comprises a nutrient component that favors the development and growth of said bacteria, and is characterized in that it also comprises L-ornithine, as a selective agent.

Advantageously, according to the invention, said culture medium comprises a nutrient component that favors the development and growth of bacteria of the genera *Salmonella* and *Shigella*, and L-ornithine, as a selective agent, and is also characterized by some or all of the following technical characteristics:
- the concentration of L-ornithine is above 10 g/L and is preferably less than or equal to 25 g/L; it is advantageously between about 15 g/L and about 20 g/L,
- said culture medium further comprises at least one additional selective agent selected from:
  - sodium deoxycholate, notably at a concentration between 0.1 g/L and 20 g/L, and even more preferably between about 1 g/L and about 10 g/L,
  - Tergitol 4, notably at a concentration between 0.5 mL/L and 10 mL/L, and even more preferably between about 1 mL/L, and about 5 mL/L,
  - bile salts, notably at a concentration between 0.1 g/L and 10 g/L, and even more preferably between about 0.5 g/L and 5 g/L,
  - crystal violet, notably at a concentration between 0.05 mg/L and 50 mg/t and even more preferably between about 0.1 mg/L and about 10 mg/L, and
  - brilliant green, notably at a concentration between 1 mg/L and 200 mg/L, and even more preferably between 10 mg/L and 50 mg/L;
- said culture medium further comprises, as selective agents:
  - L-ornithine, at a concentration between about 15 g/L and about 20 g/L,
  - sodium deoxycholate, at a concentration between about 1 g/L and about 10 g/L, and
  - optionally, Tergitol 4, at a concentration between about 0.5 mL/L and about 5 mL/L;
- said culture medium is a discriminating medium, comprising at least one chromogenic component selected from:
  - a pH color indicator (for example neutral red, phenol red, bromocresol purple, the pair bromothymol blue and acid fuchsin) capable of labeling the colonies of microorganisms fermenting at least one of the carbohydrates present in the medium.
  - a sodium thiosulfate iron(III) citrate system, allowing detection of the $H_2S$-producing bacteria,
  - chromogenic and/or fluorogenic substrates allowing the detection of particular enzyme activities;
- said culture medium comprises a nutrient component repeating that of a culture medium selected from:
  - XLD Agar (bioMérieux, France),
  - chromID® *Salmonella* Elite Agar (bioMérieux, France),
  - *Salmonella-Shigella* Agar (bioMérieux, France);
- said culture medium comprises a nutrient component and a selective component repeating those of XLD Agar, and is supplemented with:
  - L-ornithine, at a concentration between about 15 g/L and about 20 g/L,
  - optionally, X-beta-ribofuranoside, at a concentration between about 10 mg/L and about 200 mg/L,
  - optionally, an opacifier such as titanium dioxide ($TiO_2$), notably at a concentration between about 0.1 g/L and about 5 g/L, and
  - optionally, Tergitol 4, at a concentration between about 0.5 mL/L and about 5 mL/L.

The invention also covers a method of inhibition of *Escherichia coli* in which L-ornithine is used at a concentration above 10 g/L and preferably less than or equal to 25 g/L; it is advantageously between about 15 g/L and about 20 g/L. The invention also relates to the use of L-ornithine at a concentration above 10 g/L for purposes of inhibiting the growth and/or development of *Escherichia coli*.

The invention also relates to a method or procedure for enrichment and selective culture of bacteria of the genera *Salmonella* and/or *Shigella*, the use of L-ornithine for purposes of culture and/or isolation of these bacteria, as well as a culture medium, characterized by some or all of the technical Characteristics presented above and hereunder.

Other aims, features and advantages of the invention will become clear from the description that follows and the examples presented below, which aim to facilitate understanding of the invention and of its implementation. These examples are given for purposes of explanation and are not intended to limit the scope of the invention.

EXAMPLES: ELABORATION AND
EVALUATION OF THE CULTURE MEDIA
ACCORDING TO THE INVENTION

1/—Selective Media According to the Invention, Prepared on the Basis of a Composition of XLD Agar a) Preparation of Medium A1 and Medium A2

Starting from the composition of XLD Agar (bioMérieux, France), a selective isolation medium used conventionally for detecting *Salmonella* and *Shigella*, three improved culture media were prepared. They have the following compositions:

Medium composition of XLD Agar with addition of an opacifier (TiO$_2$; 0.5 g/L);
Medium A1: composition of medium T, with addition of L-ornithine (5 g/L),
Medium A2: composition of medium T, with addition of L-ornithine (10 g/L).

As L-ornithine, we may notably mention that produced and marketed by the company SIGMA-ALDRICH, USA (ref. O2375).

b) Evaluation of the Media for Detection of *Salmonella* and *Shigella*

Different species of *Salmonella* (eight serotypes including *S. enteritidis, S. Typhimurium, S. Paratyphi* A, B and C, *S. Gallinartim, S. Virchow, S. Derby*), of *Shigella* (four species including *S. sonnei, S. boydii, S. flexneri, S. dysenteriae*), as well as 15 other strains of Gram-negative bacteria (in this case strains of S, coil, and of other enterobacteria of the genera *Proteus, Citrobacter, Enterobacter* and *Pseudomonas, Acinetobacter*), all from the applicant's collection, were used.

The bacteria were suspended in physiological saline solution, and then seeded on the various media, according to the "4 quadrants" technique. The colonies formed on the agars were examined visually after 18-24 hours of incubation at 37° C.

The results obtained are summarized in Table 1 below. The inhibitions observed relate either to the size of the colonies, or the density of growth of the strains on the agars.

TABLE 1

| Medium | *Salmonella-Shigella*: strains detected/strains tested | non-*Salmonello*, non-*Shigella* strains: strains inhibited/strains tested |
|---|---|---|
| T | 16/16 | 0/15 |
| A1 | 16/16 | 7/15 |
| A2 | 16/16 | 7/15 |

These results show good sensitivity for detection of the strains of *Salmonella* and *Shigella* by all the media. However, only Medium A1 and Medium A2 are able to reduce the growth of Gram-negative bacteria other than *Salmonella* and *Shigella*.

2/—Optimization of the Concentration of L-Ornithine of the Selective Media According to the Invention, Prepared on the Basis of a Composition of XLD Medium a) Preparation of Medium A3

In view of the results presented previously, a new medium, designated Medium A3, was prepared. Its composition repeats that of Medium A2, but with double the concentration of L-ornithine (20 g/L).

b) Evaluation of Medium A3 for Detecting *Salmonella* and *Shigella*

Medium A3 was tested for detecting *Salmonella* and *Shigella*, and compared against Medium T and Medium A2. For this purpose, different species of *Salmonella* (serotypes including *S. enteritidis, S. Typhimurium, S. Paratyphi* B and C, *S. Gallinarum, S. Virchow, S. Derby*) of *Shigella* (species including *S. sonnei, S. boydii, S. flexneri, S. dysenteriae*), various strains of *Escherichia coli* (8 strains), as well as other Gram-negative bacteria (*Proteus, Enterobacter* and *Pseudomonas*), all from the applicant's collection, were used.

The bacteria were suspended in physiological saline solution, and then seeded on the media, by the 4 quadrants technique. The colonies formed on the agars were examined visually after 18-24 hours of incubation at 37° C.

The results obtained are summarized in Table 2 below. The inhibitions observed relate either to the size of the colonies, or to the density of growth of the strains on the agars.

TABLE 2

| Medium | *Salmonella-Shigella*: strains detected/strains tested | *Escherichia coli*: strains inhibited/strains tested | non-*Salmonella*, non-*Shigella*, non-*E. coli* strains: strains inhibited/strains tested |
|---|---|---|---|
| T | 14/14 | 0/8 | 0/14 |
| A2 | 14/14 | 5/8 | 6/14 |
| A3 | 14/14 | 7/8 | 8/14 |

These results show excellent sensitivity of all the media for detecting the target strains of *Salmonella* and *Shigella*, with detection of all fourteen strains for the three formulas.

However, only Medium A2 and Medium A3 are able to reduce the growth of bacterial genera other than *Salmonella* and *Shigella*, and notably for the species *E. coli*. The best selectivity is obtained at an L-ornithine concentration of 20 g/L.

3/—Selective Media According to the Invention, Prepared on the Basis of a Composition of chromID® *Salmonella* Elite Agar a) Preparation of Medium B Medium B was prepared from the composition of chromID® *Salmonella* Elite Agar (bioMérieux, France), to which L-ornithine was added to obtain a final concentration of 15 g/L. chromID® *Salmonella* Elite Agar is a chromogenic medium originally designed for selective isolation and identification of *Salmonella*, from samples of human origin.

b) Evaluation of Medium B for Detecting *Salmonella* and *Shigella*

Medium B was tested for detecting *Salmonella* and *Shigella*, and compared with Medium '1', as described above, as well as with Medium A4. The composition of the latter repeats that of Medium T, to which L-ornithine was added to obtain a final concentration of 15 g/L.

For this evaluation, different serotypes of *Salmonella* including *S. enteritidis, S. Typhimurium, S. Paratyphi* A, B and C, *S. Gallinarum, S. Virchow, S. Derby*), of *Shigella* including the species *S. sonnei, S. boydii, S. flexneri, S. dysenteriae*), different strains of *Escherichia coli* (6 strains), as well as of other Gram-negative bacteria *Proteus, Enterobacter, Citrobacter, Pseudomonas*), Gram-positive bacteria (staphylococci, enterococci) and yeasts (*Candida*), all from the applicant's collection, were used.

The bacteria were suspended in physiological saline solution, and then seeded on the media, by the 4 quadrants technique. The colonies formed on the agars were examined visually after 18-24 hours of incubation at 37° C.

The results obtained are summarized in Table 3 below. The inhibitions observed relate either to the size of the colonies, or to the rate of growth of the strains on the agars.

TABLE 3

| Medium | Salmonella-Shigella: strains detected/strains tested | Escherichia coli: strains inhibited/strains tested | non-Salmonella, non-Shigella, non-E. coli strains: strains inhibited/strains tested |
|---|---|---|---|
| T | 16/16 | 0/6 | 4/19 |
| A4 | 16/16 | 5/6 | 10/19 |
| B | 13/16 | 6/6 | 17/19 |

These results show excellent sensitivity of Medium T and of Medium A4 for detecting the strains of *Salmonella* and *Shigella*, with detection of all sixteen strains tested. Medium B makes it possible to detect thirteen strains out of the sixteen tested and shows imperfect selectivity with respect to *Salmonella* and *Shigella*.

However, only Medium A4 and Medium B are able to reduce the growth of microorganisms other than *Salmonella* and *Shigella*, notably the growth of the species coll.

4/—Optimization of the Discriminating and Chromogenic Capacity of the Selective Media According to the Invention a) Preparation of Medium C Medium C was prepared from the composition of XLD Agar (bioMérieux, France), to which the following were added: an ° pacifier (TiO$_2$; 0.5 g/L), L-ornithine (15 g/L) and a chromogenic substrate, X-beta-ribofuranoside (0.06 g/L).

b) Evaluation of Medium C for Detecting *Salmonella* and *Shigella*

Medium C was tested for detecting *Salmonella* and *Shigella*, and compared with XLD Agar.

For this evaluation, thirty strains of *Salmonella* (serotypes including *S. enteritidis, S. Typhimurium, S. Paratyphi* A, B and C, *S. Gallinarum, S. Virchow, S. Derby, S. Dublin, S. Choleraesuis, S. Infantis, S. Arizonae, S. Cubana*), forty strains of *Shigella* (species including *S. sonnei, S. boydii, S flexneri, S dysenteriae*), and fifteen other Gram-negative bacteria (*Proteus, Citrobacter, Enterobacter, E. coli* and *Pseudomonas, Acinetobacter*), all from the applicant's collection, were suspended in physiological saline solution, and then seeded on the media, by the 4 quadrants technique. The colonies formed on the agars were examined visually after 18-24 hours of incubation at 37° C.

The observations made are summarized in Table 4 below.

TABLE 4

| Strains (number of strains tested) | XLD Agar (strains detected/strains tested) | | Medium C (strains detected/strains tested) | |
|---|---|---|---|---|
| *Salmonella* (30) | 30/30 (incl. 28 colorless with black center) | colonies from 2 to 4 mm | 30/30 (incl. 28 colorless with black center) | colonies from 1.5 to 3 mm |
| *Shigella* (40) | 40/40 (colorless) | colonies from 1.5 to 5 mm | 40/40 (colored gray-blue) | colonies from 1 to 4 mm (4 strains with a lower density of growth) |
| Other Gram-negative strains (15) | 15/15 (high density of growth) | colonies from 2 to 5 mm | 10/15 | Observation of the inhibitions, based on the size of the colonies and the density of growth |

These results show excellent sensitivity of XLD Agar and Medium C, for detecting the strains of *Salmonella* and for *Shigella*, with detection of all seventy strains.

However, only Medium C is able to reduce the growth of the other Gram-negative bacteria.

5/—Optimization of the Selectivity of the Selective Media According to the Invention a) Preparation of Medium D Medium D was prepared from the composition of XLD Agar (bioMérieux, France), to which the following were added: an opacifier (TiO$_2$; 0.5 g/L), L-ornithine (15 g/L), a chromogenic substrate, X-beta-ribofuranoside (0.06 g/L) and Tergitol 4 (1.5 mL/L).

The Tergitol 4 used may notably be that manufactured and marketed by SIGMA-ALDRICH, USA (ref. Niaproof 4 N1404).

b) Evaluation of Medium D for Detecting *Salmonella* and *Shigella*

Medium D was tested for detecting *Salmonella* and *Shigella*, and compared with XLD Agar.

The following were used for this evaluation:

19 strains of *Salmonella* (3 of S, *Typhimurium*, 2 of *S. enteritidis*, 1 of S. Virchow, 3 of *S. Paratyphi* A, 3 of *S. Paratyphi* B, 2 of *S. Paratyphi* C, 1 of *S. Cubana*, 1 of *S. Dublin*, 1 of *S. Arizonae*, 1 of *S. Gallinarum*, 1 of *S. Choleraesuis*);

29 strains of *Shigella* (4 of *S. boydii*, 13 of S, *flexneri*, 12 of *S. sonnei*), 15 strains of Gram-negative bacteria, neither *Salmonella* nor *Shigella* (4 of *E. coli*, 2 of *P. vulgaris*, 1 of *P. mirabilis* 1 of *E. cloacae*, 1 of *E. aerogenes*, 1 of *P. aeruginosa*, 1 of *A. baumanii*, 1 of *E. hoshinae*, 2 of *C. braakii*, 1 of *C. youngae*).

These strains, from the applicant's collection, were suspended in physiological saline solution, and then seeded on the media, by the 4 quadrants technique. The colonies formed on the agars were examined visually after 18-24 hours of incubation at 37° C.

Table 5 below presents the observations made for cultures of pure strains.

TABLE 5

| Strains (number of strains tested) | XLD Agar (strains detected/strains tested) | | Medium C (strains detected/strains tested) | |
|---|---|---|---|---|
| Salmonella (19) | 19/19 (colorless with black center) | 15 strains forming colonies of 2 mm or more; 4 strains forming colonies of less than 2 mm | 19/19 (17 colorless with black center, 2 gray-blue) | 4 strains forming colonies of 2 mm or more; 15 strains forming colonies of less than 2 mm |
| Shigella (29) | 29/29 (all colorless) | 20 strains forming colonies of 2 mm or more; 9 strains forming colonies of less than 2 mm | 29/29 (28 colored gray-blue, 1 colorless) | 10 strains forming colonies of 2 mm or more; 19 strains forming colonies of less than 2 mm |
| Other Gram-negative strains (15) | 15/15 | 9 strains forming colonies of 2 mm or more; 9 strains forming colonies of less than 2 mm | 15/15 | 12 strains for which a notable reduction of the size of the colonies is observed |

Table 6 below presents the observations made for culture of mixed strains.

TABLE 6

| | XLD Agar | | | Medium C | | |
|---|---|---|---|---|---|---|
| | Fertility of the medium | Size | Enzyme activity | Density of growth | Size | Enzyme activity |
| S. typhimurium (ATCC 14028) + | 2.2 | 2 mm | colorless colonies with black center | 2.2 | 1.5 mm | colorless colonies with black center |
| C. braakii (ATCC15580) | 2.2 | 1.5 mm | yellow colonies | 2.2 | 1.5 mm | yellowish-green colonies |
| S. enteritidis (IM195) + | 2.3 | 2.5 mm | colorless colonies with black center | 2.3 | 1.5 mm | colorless colonies with black center |
| Sh. boydii (ATCC 8700) | 2.1 | 0.75 mm | colorless colonies | 2.3 | 0.5-0.75 mm | gray-blue colonies |
| S. paratyphi B (ATCC 10719) + | 2.3 | 2.5 mm | colorless colonies with black center | 2.3 | 2 | colorless colonies with black center |
| E. coli (ATCC 25922) | 2.1 | 1-1.5 mm | yellow | 1.1 | very fine colonies | colorless colonies |
| S. paratyphi C (ATCC 13428) + | 2.1 | 1.5-2 mm | colorless colonies with black center | 3.1 | 1.5 mm | colorless colonies with black center |
| E. coli (ATCC 12453) | 2.2 | 2.5-3 mm | colonies somewhat beige | 3.1 | 2 mm | beige colonies |

The invention claimed is:

1. A method for isolating bacteria of the genera *Salmonella* and/or *Shigella* from other bacteria contained in a biological sample, the method comprising:
    seeding at least a part of the sample in/on a culture medium selective for the bacteria of the genera *Salmonella* and/or *Shigella*, the culture medium comprising:
        a nutrient component that favors the development and growth of the bacteria of the genera *Salmonella* and/or *Shigella*; and
        L-ornithine at a concentration between about 15 g/L and about 25 g/L,
    thereby isolating the bacteria of the genera *Salmonella* and/or *Shigella* from the other bacteria contained in the biological sample.

2. The method as claimed in claim 1, wherein the culture medium further comprises at least one selective agent selected from: sodium deoxycholate, Tergitol 4, bile salts, crystal violet and brilliant green.

3. The method as claimed in claim 1, wherein the culture medium also comprises, as selective agent, sodium deoxycholate, at a concentration between about 1 g/L and about 10 g/L.

4. The method as claimed in claim 3, wherein the culture medium also comprises, as selective agent, Tergitol 4, at a concentration between about 0.5 mL/L and about 5 mL/L.

5. The method as claimed in claim 1, wherein the culture medium is a discriminating medium.

6. The method as claimed in claim 1, wherein the nutrient component comprises a culture medium selected from:
    XLD Agar, and
    *Salmonella-Shigella* Agar.

7. The method as claimed in claim 1, wherein the nutrient component comprises XLD Agar.

* * * * *